United States Patent [19]
Bauchart et al.

[11] Patent Number: 5,741,506
[45] Date of Patent: Apr. 21, 1998

[54] USE OF ACTIVE INGREDIENTS PROTECTED AGAINST DEGRADATION IN THE RUMEN AS HEPATOPROTECTORS

[75] Inventors: Dominique Bauchart, Veyre-Monton; Yves Chilliard, Ceyrat; Denys Durand, Beaumont; Dominique Gruffat, Clermont-Ferrand; Alain Ollier, Saint Genes Champanelle; Jean-Claude Robert, Neris les Bains; Peter Williams, Le Chesnay, all of France

[73] Assignee: Rhone-Poulenc Nutrition Animale, Antony, France

[21] Appl. No.: 436,115

[22] Filed: May 8, 1995

[30] Foreign Application Priority Data

May 6, 1994 [FR] France .................. 94 05617

[51] Int. Cl.⁶ .................. A61K 47/00; A23K 1/18
[52] U.S. Cl. .................. 424/439; 424/438; 426/807
[58] Field of Search .................. 424/439, 438; 426/807

[56] References Cited

U.S. PATENT DOCUMENTS

| | | | |
|---|---|---|---|
| 4,533,557 | 8/1985 | Maruyama et al. | 426/61 |
| 4,877,621 | 10/1989 | Ardaillon et al. | 424/498 |
| 4,983,403 | 1/1991 | Ardaillon et al. | 426/2 |
| 5,098,718 | 3/1992 | Ardaillon et al. | 426/2 |
| 5,462,967 | 10/1995 | Hayashi | 514/547 |

OTHER PUBLICATIONS

Aliev et al., "The Change of Lipid Classes in the Fractions of Rumen Liquor in Cows Supplemented with Choline Chloride and Methionine", Byull. Vses. Nauchno–Issled. Inst. Fiziol., Biokhim. Pitan. S–kh. Zhivotn. (1989), (2), 20–3.

French Translation of Aliev et al.

Durand et al, "Effects of Lysine and Methionine on In Vivo Hepatic Hepatic Secretion of VLDL in the High Hielding Dairy Cow", J. Dairy Sci., P403 at p. 297 (1972).

Abstract and Uncertified Translation of "Positive Effects of the Methionine (Bypass) and Choline (Bypass) Combination in the Nutrition of Ruminants", by G. Panciroli, Krmiva (1986), 28 (5–6), 139–42, CODEN: KRMIA9; ISSN: 0023–4850.

Stedman's Medical Dictionary, 24th ed., pp. 26 and 1335, 1982.

Belasco, Chemical Abstracts, vol. 93, 1981, #69298.
Aliev et al., Chemical Abstracts, vol. 112, 1990, #138099.
Lajoie et al., Chemical Abstracts, vol. 120, 1994, #7312.
Franzoni, Chemical Abstracts, vol. 118, 1993, #232693.
Ueda et al., Chemical Abstracts, vol. 119, 1993, #179771.

Primary Examiner—D. Gabrielle Phelan
Attorney, Agent, or Firm—Finnegan, Henderson, Farabow, Garrett & Dunner, L.L.P.

[57] ABSTRACT

The use of protected active ingredients, preferably methionine, protected against degradation in the rumen as a hepatoprotective agent is disclosed.

12 Claims, No Drawings

USE OF ACTIVE INGREDIENTS PROTECTED AGAINST DEGRADATION IN THE RUMEN AS HEPATOPROTECTORS

The present invention relates to the use of active ingredients which are protected against degradation in the rumen of ruminants and particularly to their effect on the hepatic state of ruminants at the beginning of lactation.

It is known from the article by Remond et al. (Ann. Zootech., 1989, 38, 129–137), the disclosure of which is incorporated herein by reference, that a protected methionine given to cows at the beginning of lactation makes it possible to obtain an increase in the quantity of milk produced during the first two weeks after birth of from 2.6 to 1.2 kg/d, and a mean increase in protein of about 27 g per day, which results in an increase in the mean protein level of milk of from 1 to 2%.

It is also known according to the article by Chilllard et al. (Reprod. Nutr. Develop., 1987, 27 (2A), 327–398), the disclosure of which is incorporated herein by reference, that at the beginning of lactation, the ingestion capacity of dairy cows is reduced; the dairy cow finds itself in a state of energy deficit and to make up for it, it mobilizes its body reserves. The triglycerides stored in the adipose tissues are hydrolysed into fatty acid and transported to the liver where they are converted to triglycerides and to ketone bodies. The capacity for recycling and exporting these nonesterified fatty acids by the liver in the form of triglycerides is low because they have to be transported by means of lipoproteins such as VLDLs (very low density lipoproteins). Now, it is known according to the article by Rayssiguier et al. (Res. Vet. Sci., 1988, 45, 389–393), the disclosure of which is incorporated herein by reference, that at the beginning of lactation the VLDLs are synthesized in a very low quantity which causes overstorage of fat at the hepatic level and thereby sometimes results in hepatic steatosis. This low synthesis of VLDLs could be due to insufficient availability of one of the lipid (cholesterol, phospholipids) or protein (apolipoprotein B) constituents.

It appeared completely surprisingly that in ruminants, the ingestion of active ingredients protected against degradation in the rumen, and the release of the active ingredients in the abomasum and/or the intestine, made it possible to reduce or prevent hepatic steatosis.

This reduction in hepatic steatosis is due, on the one hand, to an increase in the release of hepatic lipoproteins which results in an increase in the expression of the hepatic gene for apolipoprotein B (increase in the apo B mRNA) and in the intrahepatic content of apo B. Indeed, apolipoprotein, as an essential structural element for the synthesis of VLDLs, is one of the major factors limiting the production of particles high in triglycerides.

The protected active ingredients preferably used to treat these animals are chosen particularly from amino acids, amino alcohols, polyols, vitamins or mixtures of these compounds with each other. Among the amino acids, there may preferably be mentioned, with no limitation being implied, methionine and lysine. Among the amino alcohols, choline may preferably be mentioned. Among the polyols, sorbitol may preferably be mentioned, and among the vitamins, niacin may preferably be mentioned. The use of protected methionine is however more preferred. It is contemplated that, among the amino acids, lysine can be excluded, and among the amino alcohols, choline can be excluded from the active ingredients that may be used in accordance with the present invention.

Among the compounds which allow effective protection in the rumen medium and release in the abomasum or the small intestine, two main types of compounds can be mentioned. Some of these compounds allow a protection and a release which is caused solely by a chemical phenomenon, due to the difference in the value of the pH between the rumen (5–6) and the abomasum (2–3). There may be mentioned in this category, pH-sensitive polymers such as copolymers of styrene and vinylpyridine mixed with fatty substances such as fatty acids, hydrogenated vegetable or animal oils. Numerous patents such as the patents U.S. Pat. No. 4,877,621 or U.S. Pat. No. 4,832,967, the disclosures of which are incorporated herein by reference, describe compositions containing such compounds. These compositions allow an excellent protection in vivo and in vitro of nutritive or medicinal substances and a good release of the active ingredients. Their only disadvantage is the fact that they contain a synthetic chemical product, which from a dietary and ecological perspective is not always highly appreciated both from the point of view of the administrative authorities for placing on the market and from that of consumers.

In this first category of compositions where the release of the active ingredient is caused solely by a chemical phenomenon, compositions based on chitosan and carboxylic acids may also preferably be mentioned. These compositions are for example described in the French patent published under number 2,524,269, the disclosure of which is incorporated herein by reference. These compositions contain a quantity of active ingredients which is always less than 60% by weight and more preferably of the order of 30% so as to allow a protection in the rumen of the order of 80 to 90% over 24 hours. These compositions contain, in addition, one or more pH-sensitive inorganic fillers in substantial quantity (10 to 20% by weight).

A second category of patents describes compositions using the enzymatic hydrolysis properties of some natural compounds such as zein. Among these patents, there may be mentioned U.S. Pat. Nos. 4,983,403 and 5,098,718 and European Patent Application No. EP 0,406,041, the disclosures of which are incorporated herein by reference.

The present invention describes the effect of the active ingredients previously described (amino acids, amino alcohols, polyols and vitamins), protected against degradation in the rumen and released in the abomasum or the small intestine, on the release of hepatic lipoproteins high in triglycerides as well as the effect on the synthesis of apolipoprotein B mRNA and on the release of apolipoprotein B at the hepatic level.

In accordance with the present invention, 15–45 grams of protected active ingredient can be administered to prevent or treat hepatic steatosis in ruminants. Typically, 75–80% of protected active ingredient will result in digestible active ingredient.

The present invention will be more fully described with the aid of the following examples which should not be considered as limiting the invention.

EXAMPLE 1

The object of the present example is to evaluate to what extent a supplementation with methionine, protected against fermentation in the rumen, prepared especially according to patent U.S. Pat. No. 4,877,621, the disclosure of which is incorporated herein by reference, can limit hepatic steatosis and ketosis in fatty cows at the beginning of lactation receiving a ration having a low energy concentration.

Materials and Methods

1-Animals

Fifteen cows were divided into 2 batches balanced with respect to the calving date, the body condition score, the live weight 3 months before calving and the maximum milk production of the preceding lactation.

The two batches were the following: control without methionine (T, 8 cows); batch receiving protected methionine (M, 7 cows), one having had to be removed from the experiment at the beginning of the post-experiment part (42 days after the calving).

2-Diet a) End of gestation

The animals received maize silage ad libitum, with concentrate according to the following procedure, W(-4) to W(-1) indicating the weeks before calving:

| kg | W(-4) and W(-3) | W(-2) | W(-1) |
|---|---|---|---|
| Concentrate | 0.5 | 1.5 | 2.5 |
| Tanned soyabean cakes | 1 | 1.0 | 1.0 |
| Untanned soyabean cakes | 0.5 | 0.5 | 0.5 |

The calcium supply was limited (100 g/d then removal 3 weeks before calving) and a supplement of about 1 kg of hay was distributed per day.

b) Beginning of lactation

The animals received, in one meal per day, a balanced ration of constant composition for the first three months of lactation, which contained 75% of maize silage, 20% of tanned soyabean cake and 5% of untanned soyabean cake. Vitamin-enriched mineral concentrate (200 g/d) and hay (1 kg/d) were added.

Protected methionine (22 g/d)

Protected methionine (22 g/d), from which approximately 75–80% of digestable methionine is obtained, was distributed in the morning, after being starved, in a bucket with 200 g of untanned cake, for 5 days, to all the cows (15) which were three to four weeks before birth; then daily to the cows of the M group from the 3rd or 5th day after birth (on day 3 to 5 of lactation), up to the 6th week of lactation inclusive (42 days).

Assay of the Lipoproteins

Separation of the major classes of lipoproteins

The VLDLs (very low density lipoproteins) were separated from 20 ml of plasma by flotation ultracentrifugation: 40,000 rpm for 16 hours at 15° C.

The IDLs, LDLs, lHDLs and hHDLs (lipoproteins of intermediate, low density, light high density and heavy high density) were separated by density gradient at 39,000 rpm for 46 hours and at 15° C., according to the technique described by Chapman, Golstein Lagrange and Laplaud, J. Lip. Res., 22, 339–358 (1981) and adapted by Bauchard et al., J. Lip. Res., 30, 1499–1514 (1989), the disclosures of which are incorporated herein by reference.

There were thus obtained 5 classes of lipoproteins:
VLDL: d<1.018 g/ml
IDL: 1.018 g/ml<d<1.026 g/ml
LDL: 1.026 g/ml<d<1.060 g/ml
lHDL: 1.060 g/ml<d<1.091 g/ml
hHDL: 1.091 g/ml<d<1.180 g/ml These different lipoprotein fractions were then dialysed at 4° C. for 7 hours with a microdialysis system in order to remove the KBr.

Separation of the true LDLs and the very light HDLs (vlHDL) in the density zone 1.040–1.090 g/ml In the first instance, the size heterogeneity of the particles in the density zone 1.040–1.090 g/ml was checked by acrylamide gradient gel electrophoresis (PAA gel: 2.5–16%) of all the animals at each of the different stages studied. After having verified the homogeneity of the animals, the plasmas were grouped according to stage and according to treatment, and then the lipoprotein particles were isolated by flotation ultracentrifugation according to the procedure described by Laplaud et al., J. Lip. Res., 32, 1429–1439 (1991), the disclosure of which is incorporated herein by reference, in the density zone 1.040–1.090 g/ml. These types of HDL and LDL lipoproteins were then separated by affinity chromatography on a heparin-Sepharose column which allowed the separation and quantification of the LDL particles (without contamination by the HDLs) called "true LDLs" on the one hand, and the HDLs not contaminated by LDLs on the other. These particles were then analysed, like the other lipoprotein classes separated on a gradient, especially the chemical composition.

Determination of the chemical composition

On each of the plasma lipoprotein fractions as on the total plasma, the apolipoproteins A-I and B were assayed by radial immunodiffusion according to the Mancini method adapted by Auboiron et al., Reprod. Nutr. Develop., 2, 2275 (1989), the disclosure of which is incorporated herein by reference. The total protein of the lipoprotein fractions was assayed by colorimetry by the colorimetric method using the reagent based on bicinchroninic acid (BCA, Pierce, Ill., USA).

Assay of the hepatic apo B mRNA

The total RNA was isolated from liver biopsies (about 200 mg) with guanidine thiocyanate/phenol-chloroform according to the method described by Chornczynski and Sacchi, Ann. Biochem. 162, 156–159 (1987), the disclosure of which is incorporated herein by reference.

The quantification of the ado B mRNA was carried out according to the following method: 70 g of each total RNA extract were denatured in the presence of formaldehyde and deposited in ½ serial dilutions on a nitrocellulose membrane using a Dot-Blot apparatus (Schleicher & Schuell, SRC 26 D Minifold 1), that is to say, 4 deposits of about 30, 15, 7.5 and 3.75 µg for each RNA extract. The hybridization was carried out with a probe synthesized from a cDNA fragment of human apo B purified in the laboratory and labelled with ($\alpha^{32}$P)dCTP (deoxycytidyltriphosphate) by random priming. The abundance of ado B mRNA was calculated by densiometric analysis of autoradiographs obtained after exposing the membranes for 16 hours at -80° C.

Comparison between the different autoradiographs being impossible, it was chosen to deposit, on the same membrane, the total RNA corresponding to the different stages of sampling (W1, W2, W4 and W12) of 5 cows (2 controls and 3 methionines or vice versa). This allowed the variation of the contents of apo B mRNA to be determined during the beginning of lactation and this variation between the cows of the control and experimental batches to be compared.

Assay of intrahepatic apolipoprotein B

The total intrahepatic protein was extracted by homogenization of liver fragments collected by biopsy (50 mg) in a lysis solution with a high concentration of detergents (sodium deoxycholate, Triton X-100) and of protease inhibitors (benzamidine, PMSF, leupeptin, pepstatin).

The total intrahepatic protein extracted was quantified by colorimetric assay according to the Bradford method (1976). Comparable quantities (100 µg) of total protein were deposited on a polyacrylamide gel gradient (3–7.5%) under denaturing conditions. After electrophoretic migration, the proteins were transferred onto nitrocellulose membrane by electrotransfer. These membranes were incubated in the presence of anti-bovine apo B rabbit polyclonal antibody.

The binding of the antibody onto the band corresponding to apo B was revealed by incubating the membrane in the presence of $^{125}$iodine-labelled protein A. The intrahepatic apo B contents were calculated by densiometric analysis using the autoradiographs obtained after exposing the membranes for 16 h at −80° C.

3- Plasma lipids and apolipoproteins (Table 1)

From the first week of lactation, the concentration of circulating nonesterified fatty acids was very high and it was maintained at the W2 stage. These levels then decreased by nearly 50% (P<0.05) from W2 to W4 (during the postprandial period), reaching very low values in W12. The contents of free cholesterol, of esters of cholesterol and phospholipids in the plasma underwent a reverse trend, their levels increasing substantially between W1 and W12, these levels being multiplied by the factors 5, 3 and 2 respectively. On the other hand, the triglyceridaemia remained constant during this entire period. No significant difference was observed between the 2 batches for the entire lipid fractions studied.

The level of total plasma apolipoprotein B did not vary between W1 and W2 and remained close to 4 mg/dl, then increased up to a value of 11 mg/dl at the W12 stage. This variation was comparable for the 2 batches (control and methionine).

The level of total plasma apolipoprotein A-I increased, as in the case of apo B, mainly between the W2 and W12 stages, reaching on average 100 mg/dl in W12. On the other hand, a slight difference was observed in the form of variation between our 2 batches indeed, the increase in the level of apo A-I was essentially observed between the W2 and W4 stages for the "methionine" batch whereas this increase was much more gradual in the "control" batch. In spite of this difference in the form of variation, no significant difference in their plasma content was observed between the 2 batches regardless of the lactation stage studied.

(methionine diet M, n=7); W1=3–5 d; W2=10–12 d; W4=24–26 d; W12=71–89 d after calving.

The plasma lipid concentrations were compared within the same batch by the "t" test in the case of paired series. The values assigned 2 different letters, i.e., a, b, c or d, are significantly different at the 5% threshold.

4-Plasma lipoproteins

The overall variation of the different lipoprotein families shows that the plasma concentrations of VLDLs, IDLs and heavy HDLs (hHDLs) were barely modified during the first 12 weeks of lactation. On the other hand, the plasma levels of LDLs and light HDLs (lHDLs) increased very substantially between W1 and W12 (Table 2). The lipid composition of these two lipoprotein families was only barely modified.

TABLE 2

| | | Weeks after calving | | | |
|---|---|---|---|---|---|
| | | W1 | W2 | W4 | W12 |
| "True" LDLs | C | 21.4 ± 3.4$^a$ | 22.8 ± 3.1$^a$ | 34.9 ± 5.5$^b$ | 63.0 ± 5.8$^c$ |
| | M | 14.6 ± 2.9$^a$ | 18.2 ± 4.0$^a$ | 24.0 ± 5.9$^b$ | 59.3 ± 6.4$^c$ |
| vlHDL | C | 6.8 ± 5.5$^{ab}$ | 0.3 ± 2.7$^a$ | 17.4 ± 8.2$^b$ | 71.0 ± 19.0$^c$ |
| | M | 3.5 ± 4.1$^a$ | 5.4 ± 2.7$^{ab}$ | 27.4 ± 10.3$^b$ | 98.0 ± 38.4$^c$ |

Variation of the concentration of "true" LDLs and very light HDLs (vlHDL) type lipoproteins (mg/dl: mean±SE) isolated by density gradient ultra-centrifugation and then by affinity chromatography on heparin-Sepharose in dairy cows during the beginning of lactation receiving a diet based on maize silage (control diet C, n=8) or the same diet supplemented with protected methionine (methionine diet M, n=7) from 4 to 6 days up to days after calving.

The plasma lipid concentrations were compared within the same batch by the "t" test in the case of paired series. The values assigned 2 different letters, i.e., a, b, c or d, were significantly different at the 5% threshold.

TABLE 1

| Plasma compounds | | Weeks atter calving | | | |
|---|---|---|---|---|---|
| | | W1 | W2 | W4 | W12 |
| NEFA | C | 28.6 ± 3.8$^a$ | 26.7 ± 5.1$^a$ | 13.2 ± 2.2$^b$ | 2.8 ± 0.8$^c$ |
| | M | 26.1 ± 4.4$^a$ | 22.8 ± 2.8$^a$ | 16.2 ± 2.6$^b$ | 2.3 ± 0.6$^c$ |
| FC | C | 3.3 ± 0.5$^a$ | 5.0 ± 1.1$^a$ | 9.7 ± 2.1$^b$ | 16.5 ± 2.1$^c$ |
| | M | 4.3 ± 0.8$^a$ | 5.2 ± 1.2$^a$ | 10.7 ± 2.7$^b$ | 16.8 ± 2.1$^c$ |
| EC | C | 75.9 ± 5.1$^a$ | 105.7 ± 9.4$^b$ | 156.8 ± 13.3$^c$ | 205.2 ± 11.9$^d$ |
| | M | 72.8 ± 6.7$^a$ | 97.6 ± 6.0$^b$ | 160.7 ± 9.1$^c$ | 213.7 ± 7.6$^d$ |
| PL | C | 86.8 ± 4.1$^a$ | 120.5 ± 13.1$^b$ | 143.5 ± 12.1$^b$ | 154.1 ± 12.5$^b$ |
| | M | 85.3 ± 5.5$^a$ | 121.3 ± 23.8$^a$ | 132.6 ± 15.5$^a$ | 187.9 ± 13.5$^b$ |
| TG | C | 17.8 ± 1.9 | 17.8 ± 1.2 | 16.6 ± 0.8 | 17.5 ± 1.0 |
| | M | 16.4 ± 1.2 | 16.5 ± 1.0 | 19.8 ± 3.0 | 17.3 ± 0.6 |
| apo B | C | 3.8 ± 1.0$^a$ | 4.7 ± 1.0$^a$ | 6.8 ± 1.9$^b$ | 10.7 ± 2.4$^c$ |
| | M | 3.7 ± 1.5$^a$ | 3.7 ± 1.3$^a$ | 4.8 ± 1.7$^a$ | 11.2 ± 3.1$^b$ |
| Apo A-I | C | 50.4 ± 7.1$^a$ | 63.1 ± 8.3$^b$ | 80.1 ± 15.3$^c$ | 100.7 ± 16.8$^d$ |
| | M | 70.6 ± 10.9$^a$ | 69.1 ± 5.1$^a$ | 100.8 ± 14.5$^b$ | 106.9 ± 5.9$^b$ |

Table: Variation of the contents of lipids (NEFA, Nonesrefilled Fatty Acids; FC, Free Cholesterol; EC, Esters of Cholesterol; PL, Phospholipids; TG: Triglycerides) and of apolipoproteins A-I and B (Apo A-I, Apo B) in plasma (mg/dl; mean±SE) in dairy cows during the beginning of lactation receiving a diet based on maize silage (control diet C, n=8) or the same diet supplemented with protected methionine from 4 to 6 days up to 42 days after calving In contrast, the respective contents of apolipoproteins A-I and B of the LDLs isolated (Table 3) between the densities 1.020–1.060 g/ml vary substantially with the lactation stage studied. Thus, the concentration of apo B increased from 3 to 9 mg/dl between W1 and W12 and that of apo A-I from 2 to 16 mg/dl. The contribution of apolipoprotein A-I to the total content of the particles in this zone increased from 7 to 10% and was more rapid over time for the group receiving methionine.

TABLE 3

| | | LDL (W1) | | LDL (W2) | | LDL (W4) | | LDL (W12) | |
|---|---|---|---|---|---|---|---|---|---|
| | | C | M | C | M | C | M | C | M |
| Lipoproteins | mg/ml | 28.2 ± 7.7 | 18.1 ± 4.6 | 23.1 ± 2.7 | 23.6 ± 2.9 | 52.3 ± 9.1 | 51.4 ± 14 | 134.0 ± 15.8 | 157.3 ± 34 |
| Apo B | mg/dl | 3.2 ± 0.5 | 2.2 ± 0.4 | 3.4 ± 0.5 | 2.7 ± 0.6 | 5.2 ± 0.8 | 3.6 ± 0.9 | 9.5 ± 0.9 | 8.9 ± 1.0 |
| | % tot. lipo. | 13.9 ± 2.4 | 14.9 ± 3.9 | 15.4 ± 1.6 | 11.4 ± 1.8 | 10.8 ± 1.3 | 8.1 ± 1.5 | 7.9 ± 1.4 | 7.0 ± 1.5 |
| Apo A-I | mg/dl | 1.7 ± 0.4 | 1.6 ± 0.5 | 1.3 ± 0.3 | 2.2 ± 0.2 | 5.1 ± 1.6 | 5.1 ± 1.7 | 14.2 ± 2.8 | 19.5 ± 8.0 |
| | % tot. lipo. | 6.9 ± 1.2 | 8.7 ± 0.8 | 5.3 ± 0.8 | 10 ± 1.5 | 8.7 ± 1.4 | 10.6 ± 1.9 | 10.1 ± 0.8 | 10.4 ± 2.0 |

5-Hepatic levels of Apo B mRNA (Tables 4 and 5)

The results presented relate to the 8 cows of the control batch, and the 6 or 7 cows of the methionine batch (7 during the period of treatment with protected methionine and 6 over the entire trial).

The quantification of the hepatic apo B mRNA was carried out by Dot-Blot analysis. The variations of the levels of apo B mRNA (arbitrary units/µg of RNA) between 2 consecutive stages of sampling (W2-W1; W4-W2; W12-W4) were calculated for the two batches of cows (Table 4). The large variations in apo B mRNA levels between the animals and the differences in signal intensity existing between the autoradiographs caused the appearance of large standard deviations during this calculation. We can however note a significant increase in the intrahepatic apo B mRNA levels between the W1 and W2 stages for the methionine batch (6 cows out of 7, P<0.035 or 6 cows out of 6, P<0.02) and between the W2 and W4 stages for the control batch (7 cows out of 8, P<0.06).

TABLE 4

| | Variation of the hepatic contents of apo B mRNA | | |
|---|---|---|---|
| Batches | W2-W1 | W4-W2 | W12-W4 |
| Control (n = 8) | 910 ± 607 | 1359 ± 698* | 658 ± 974 |
| Methionine (n = 7) | 3505 ± 920** | 183 ± 1407 | — |
| Methionine (n = 6) | 4109 ± 778*** | 263 ± 454 | 1428 ± 1358 |

Variation of the intrahepatic contents of apo B mRNA (arbitrary units/µg of total RNA, ±SE) between 2 consecutive stages of sapling in dairy cows at the beginning of lactation receiving a diet based on maize silage (control diet C, n=8) or the same diet supplemented with protected methionine (methionine diet M, n=7 or n=6) from 3 to 5 days up to 42 days after calving (W1=3–5 d; W2=10–12 d; W4=24–26 d; W12=71–89 d).

The values were significantly different from 0 at the 6% (*), 3.5% () or 2% (*) threshold (sign test).

With the aim of eliminating the deviations induced by the differences in signal intensity existing between the autoradiographs, the ratio of the hepatic levels of apo B mRNA which were measured between two consecutive weeks of sampling (W2/W1; W4/W2; W12/W4) was calculated (Table 5). This ratio made it possible to detect a significant increase (P<0.01) in the apo B mRNA of 50% between the W1 and W2 stages in the methionine batch whereas no significant variation was observed for the control batch for this same period.

TABLE 5

| | Ratio of the hepatic levels of apo B mRNA | | |
|---|---|---|---|
| Batches | W2/W1 | W4/W2 | W12/W4 |
| Control (n = 8) | 1.08 ± 0.07ª | 1.20 ± 0.10 | 1.10 ± 0.09 |
| Methionine (n = 7) | 1.50 ± 0.10ᵇ | 0.96 ± 0.12 | — |
| Methionine (n = 6) | 1.58 ± 0.05ᵇ | 0.98 ± 0.13 | 1.27 ± 0.17 |

The ratio of the intrahepatic contents of apo B mRNA (arbitrary units/µg of total RNA, ±SE) between 2 consecutive stages of sampling in dairy cows at the beginning of lactation receiving a diet based on maize silage (control diet C, n=8) or the same diet supplemented with protected methionine (methionine diet M, n=7 or n=6) from 3 to 5 days up to 42 days after calving (W1=3–5 d; W2=10–12 d; W4=24–26 d; W12=71–89 d).

The values assigned two different letters are significantly different at the 1% threshold 6- Variation of the hepatic contents of apo B (Tables 6 and 7)

The quantification of intrahepatic apo B was carried out by Western blot analysis. The variations of the levels of apo B (arbitrary units/$10^9$ cells) between 2 consecutive stages of sampling (W2-W1; W4-W2; W12-W4) were calculated for the two batches of cows (Table 6). The large variations in apo B levels between the animals and the differences in signal intensity existing between autoradiographs caused the appearance of large standard deviations during this calculation. We can however note a significant increase in the intrahepatic apo B levels (according to the sign test) between the W2 and W1 stages for the methionine batch (p<0.01) and between the W4 and W2 stages for the control batch (p<0.035).

TABLE 6

| | Variation of the hepatic contents of apo B | | |
|---|---|---|---|
| Batches | W2/W1 | W4/W2 | W12/W4 |
| Control (n = 8) | −0.56 ± 6.9 | 19.10 ± 5.4 | 89.2 ± 21** |
| Methionine (n = 7) | 18.20 ± 2.9** | 7.67 ± 7.2 | — |
| Methionine (n = 6) | 14.00 ± 3.6** | 3.92 ± 7.1 | 76.5 ± 23** |

Variation of the intrahepatic contents of apo B (arbitrary units/$10^9$ cells, ±SE) between 2 consecutive stages of sampling in dairy cows at the beginning of lactation receiving a diet based on maize silage (control diet C, n=8) or the same diet supplemented with protected methionine (methionine diet M, n=7 or n=6) from 3 to 5 days up to 42 days after calving (W1=3–5 d; W2=10–12 d; W4=24–26 d; W12=71–89 d).

The differences were significantly different from 0 at the 3.5% threshold (*) or at the 1% threshold (**) (U test).

With the aim of eliminating the differences in signal intensity exhibiting between autoradiographs, the ratio of the hepatic levels of apo B between 2 consecutive weeks of sampling (W2/W1; W4/W2; W12/W4) was calculated (Table 7). This ratio made it possible to detect a significant increase (p<0.01) in the level of apo B of 68% between the W2 and W1 stages in the methionine batch whereas no significant variation was observed for the control batch for this same period.

TABLE 7

Ratio of the hepatic levels of apo B

| Batches | W2/W1 | W4/W2 | W12/W4 |
|---|---|---|---|
| Control (n = 8) | 1.07 ± 0.12$^a$ | 1.52 ± 0.20 | 2.49 ± 0.40 |
| Methionine (n = 7) | 1.68 ± 0.09$^b$ | 1.22 ± 0.16 | — |
| Methionine (n = 6) | 1.66 ± 0.10$^b$ | 1.14 ± 0.16 | 2.70 ± 0.54 |

Ratio of the intrahepatic contents for apo B (arbitrary units/µg of total RNA) between 2 consecutive stages of sampling in dairy cows at the beginning of lactation receiving a diet based on maize silage (control diet C, n=8) or the same diet supplemented with protected methionine (methionine diet M, n=7 or n=6) from 3 to 5 days up to 42 days after calving (W1=3–5 d; W2=10–12 d; W4=24–26 d; W12=71–89 d).

The values assigned two different letters were significantly different at the 1% threshold.

EXAMPLE 2

Example 1 was reproduced on 16 cows (6 controls and 10 for the experiments). The cows received the same basic diet as in Example 1, and received, for the cows (M), 40 g of protected methionine (about 28 g of digestible methionine), and for the cows (M+L), 18 g of protected methionine (13 g of digestible methionine) and 100 g of protected methionine/lysine (50 g of digestible lysine and 15 g of digestible methionine).

The results relating to the blood analyses are indicated in Table 8, the results relating to the hepatic contents of triglycerides, apo B mRNA and apo B are indicated in Tables 9, 10 and 11.

TABLE 8

Contents of blood metabolites in the 2nd and 4th weeks of lactation (1)

| | | Control (n = 6) | Methionine (n ± 5) | Meth. + Lysine (N = 5) |
|---|---|---|---|---|
| NEFA (mN) | W2 | 0.68 (±0.15) | 0.66 (±0.14) | 0.47 (±0.15) |
| | W4 | 0.48 (±0.11) | 0.45 (±0.11) | 0.33 (±0.11) |
| Glucose (mg/dl) | W2 | 37 (±3) | 42 (±4) | 42 (±4) |
| | W4 | 40 (±4) | 36 (±4) | 40 (±4) |
| Lactate (mM) | W2 | 0.54 (±0.13) | 0.79 (±0.14) | 0.88 (±0.14)$^a$ |
| | W4 | 0.85 (±0.18) | 0.63 (±0.20) | 0.56 (±0.20) |
| β-hydroxy-butyrate (mM) | W2 | 2.78 (±0.42) | 1.86 (±0.45)$^b$ | 2.26 (±0.50) |
| | W4 | 3.01 (±0.70) | 2.93 (±0.75) | 2.93 (±0.83) |
| Acetone (mg/dl) | W2 | 6.1 (±1.1) | 2.2 (±1.3)$^c$ | 3.0 (±1.3)$^d$ |
| | W4 | 5.7 (±2.7) | 4.6 (±2.9) | 5.9 (±3.0) |

TABLE 8-continued

Contents of blood metabolites in the 2nd and 4th weeks of lactation (1)

| | | Control (n = 6) | Methionine (n ± 5) | Meth. + Lysine (N = 5) |
|---|---|---|---|---|
| Urea (mg/dl) | W2 | 37.1 (±3.3) | 36.5 (±4 4) | 28.5 (±3.5)$^e$ |
| | W4 | 39.2 (±3.4) | 37.4 (±4.6) | 32.7 (±3.6) |

(1) Values adjusted as a function of the first week covariable:
$^a$Different from the control batch (P < 0.10)
$^b$Different from the control batch (P < 0.17)
$^c$Different from the control batch (P < 0.05)
$^d$Different from the control batch (P < 0.11)
$^e$Different from the control batch (P < 0.11)

TABLE 9

Hepatic contents of triglycerides (mg/g of frozen fresh liver)

| Weeks after calving | W1 | W2 | W4 |
|---|---|---|---|
| Control (n = 6) | 54.5 ± 12.5 | 70.6 ± 19.9 | 55.2 ± 15.3 |
| Methionine (n = 5) | 34.6 ± 4.1$^a$ | 67.6 ± 11.8$^b$ | 36.4 ± 9.7$^a$ |
| Met. + lys. (n = 5) | 36.2 ± 5.9 | 46.2 ± 13.2 | 25.3 ± 9.8 |

$^{a,b}$: P < 0.05. t Test for comparison of mean values for the same line in the case of paired series.

The methionine and/or the lysine were distributed after week W1.

TABLE 10

Hepatic contents of apo B mRNA (A.U./µg of total RNA)

| Weeks after calving | W1 | W2 | W4 |
|---|---|---|---|
| Control (n = 6) | 134.8 ± 20.7 | 150.8 ± 21.9 | 130.1 ± 17.4 |
| Methionine (n = 5) | 101.3 ± 18.4$^a$ | 83.5 ± 11.4$^a$ | 151.6 ± 30.1$^b$ |
| Met. + lys. (n = 5) | 97.9 ± 118.3$^c$ | 155.9 ± 19.2$^a$ | 123.2 ± 16.4$^b$ |

$^{a,b}$: P < 0.05; $^{a,c}$: P < 0.10. t Test for comparison of mean values for the same line in the case of paired series.

The methionine and/or the lysine were distributed after week W1.

TABLE 11

Hepatic contents of apo B (A.U./10$^9$ cells)

| Weeks after calving | W1 | W2 | W4 |
|---|---|---|---|
| Control (n = 6) | 53.94 ± 6.25 | 50.6 ± 7.2 | 66.4 ± 17.8 |
| Methionine (n = 5) | 45.5 ± 8.2$^a$ | 41.4 ± 12.1$^a$ | 65.6 ± 12.6$^b$ |
| Met. + lys. (n = 5) | 46.2 ± 7.7$^c$ | 65.7 ± 9.6$^d$ | 99.8 ± 41.2$^d$ |

$^{a,b}$: P < 0.03; $^{c,d}$: P < 0.2. t Test for comparison of mean values for the same line in the case of paired series.

The methionine and/or the lysine were distributed after week W1.

The contents of blood metabolites (Table 8) show only few significant effects of the treatments. It was however observed that in the second week of lactation, the treatment with methionine significantly reduced the contents of ketone bodies (β-hydroxybutyrate and acetone). Similar but less significant trends are observed with the methionine+lysine treatment.

The Control batch showed fairly high hepatic levels of triglycerides (TG) in week W1 (first week after calving) and tended to increase in week W2 (+30%, NS) and then to decrease slightly by the same amount in week W4 (-22 NS %). The cows were, at the beginning of lactation, in a state of steatosis (54.5-70.6 mg of TG/g of liver).

In the batch supplemented with methionine, the hepatic contents of TG were lower in week W1 (before treatment with methionine) than in the Control batch but increased substantially in week W2 (+95%, P<0.05), reaching values comparable to those observed in the Control batch. However, the lipid infiltration decreased significantly in week W4 (-46%, P<0.05). A significant increase both in the intrahepatic levels of apo B mRNA (+82%, P<0.05) and of apo B (+58%, P<0.03) appeared in week 4 compared with week W2.

In the batch supplemented with methionine and lysine, the hepatic levels of TG in week W1 (before treatment with methionine+lysine) were comparable to those observed for the batch supplemented with methionine. However, no substantial increase was observed in the level of TG in week W2, contrary to the batch supplemented with methionine alone. The decrease between weeks W2 and W4 lead to a low level of lipid infiltration in week W4. An increase in the intrahepatic levels of apo B mRNA (+59%, P<0.10) and of apo B (+42%, P<0.20) appeared from week W2 for all the cows in spite of a high standard deviation.

What is claimed is:

1. A method for the prevention or treatment of hepatic steatosis in ruminants, said method comprising administering to a ruminant in an amount effective to prevent or treat hepatic steatosis a composition containing at least one active ingredient, said at least one active ingredient being selected from amino acids, polyols, amino alcohols, and vitamins, and said at least one active ingredient being protected from degradation in the rumen by a composition comprising a pH-sensitive polymer and a fatty substance or a composition stable in the rumen and subject to enzymatic degradation in the abomasum or small intestine.

2. The method according to claim 1, wherein said composition reduces the content of triglycerides in the liver.

3. The method according to claim 1, wherein said composition reduces the content of ketone bodies in the blood stream.

4. The method according to claim 1, wherein said composition increases the synthesis of hepatic apoliprotein B.

5. The method according to claim 1, wherein said amino acid is methionine.

6. The method according to claim 1, wherein said at least one active ingredient is protected by a mixture which comprises a vinylpyridine/styrene copolymer and a fatty acid.

7. The method according to claim 1, wherein said at least one active ingredient is protected by a natural polymer based on chitosan.

8. The method according to claim 6, wherein said at least one active ingredient is protected by a polymer based on zein.

9. The method according to claim 1, wherein said at least one active ingredient for the purpose of preventing or treating hepatic steatosis is present in said protected composition in an amount ranging from 15 to 45 grams/day.

10. The method according to claim 9, wherein 75-80% of said protected active ingredient is digestible active ingredient.

11. The method according to claim 9, wherein the protected composition is administered to ruminants in need of treatment of hepatic steatosis.

12. The method according to claim 11, wherein said ruminants in need of treatment are at the beginning of lactation.

* * * * *